United States Patent [19]

Imai

[11] 4,438,287
[45] Mar. 20, 1984

[54] PREPARATION OF ALCOHOLS

[75] Inventor: Tamotsu Imai, Mount Prospect, Ill.

[73] Assignee: UOP Inc., Des Plaines, Ill.

[21] Appl. No.: 411,213

[22] Filed: Aug. 25, 1982

Related U.S. Application Data

[63] Continuation-in-part of Ser. No. 248,385, Mar. 27, 1981, abandoned, which is a continuation-in-part of Ser. No. 93,461, Nov. 13, 1979, abandoned.

[51] Int. Cl.³ .............................................. C07C 29/16
[52] U.S. Cl. .................................. 568/909; 568/821; 568/831; 568/838; 568/839; 585/660
[58] Field of Search ............... 568/909, 821, 831, 838, 568/839; 585/660

[56] References Cited

U.S. PATENT DOCUMENTS

| | | | |
|---|---|---|---|
| 2,454,227 | 11/1948 | Smith et al. | 568/894 |
| 3,536,632 | 10/1970 | Kroll | 568/894 |
| 3,631,111 | 12/1971 | Tucci | 568/909 |
| 3,857,895 | 12/1974 | Booth | 568/909 |
| 3,912,785 | 10/1975 | Suzuki | 568/862 |
| 4,045,492 | 8/1977 | Kniese et al. | 568/909 |
| 4,072,602 | 2/1978 | Hayes | 585/660 |
| 4,210,769 | 7/1980 | Antos | 585/660 |
| 4,292,196 | 9/1981 | Homeier et al. | 568/909 |
| 4,313,020 | 1/1982 | Antos | 585/660 |
| 4,376,225 | 3/1983 | Vora | 585/660 |

FOREIGN PATENT DOCUMENTS

| | | | |
|---|---|---|---|
| 517815 | 10/1955 | Canada | 568/909 |
| 1397293 | 6/1975 | United Kingdom | 585/660 |
| 1601818 | 11/1981 | United Kingdom | 568/909 |

*Primary Examiner*—J. E. Evans
*Attorney, Agent, or Firm*—James R. Hoatson, Jr.; Raymond H. Nelson; William H. Page, II

[57] ABSTRACT

Alcohols may be prepared in a combination process by subjecting an aliphatic paraffinic hydrocarbon feed stream to a dehydrogenation reaction and thereafter subjecting the reaction product mix comprising a mixture of aliphatic paraffinic hydrocarbons and aliphatic olefinic hydrocarbons, without separating the olefins in the product mix from the paraffins, to a hydroformylation reaction. The hydroformylation reaction is effected by treating said product mix with carbon monoxide and hydrogen in the presence of a catalyst comprising a rhodium-containing compound and a promoter comprising a trialkyl-substituted monoamine, all three of said alkyl moieties being substituted to the nitrogen of said amine to selectively prepare the desired alcohols.

11 Claims, 1 Drawing Figure

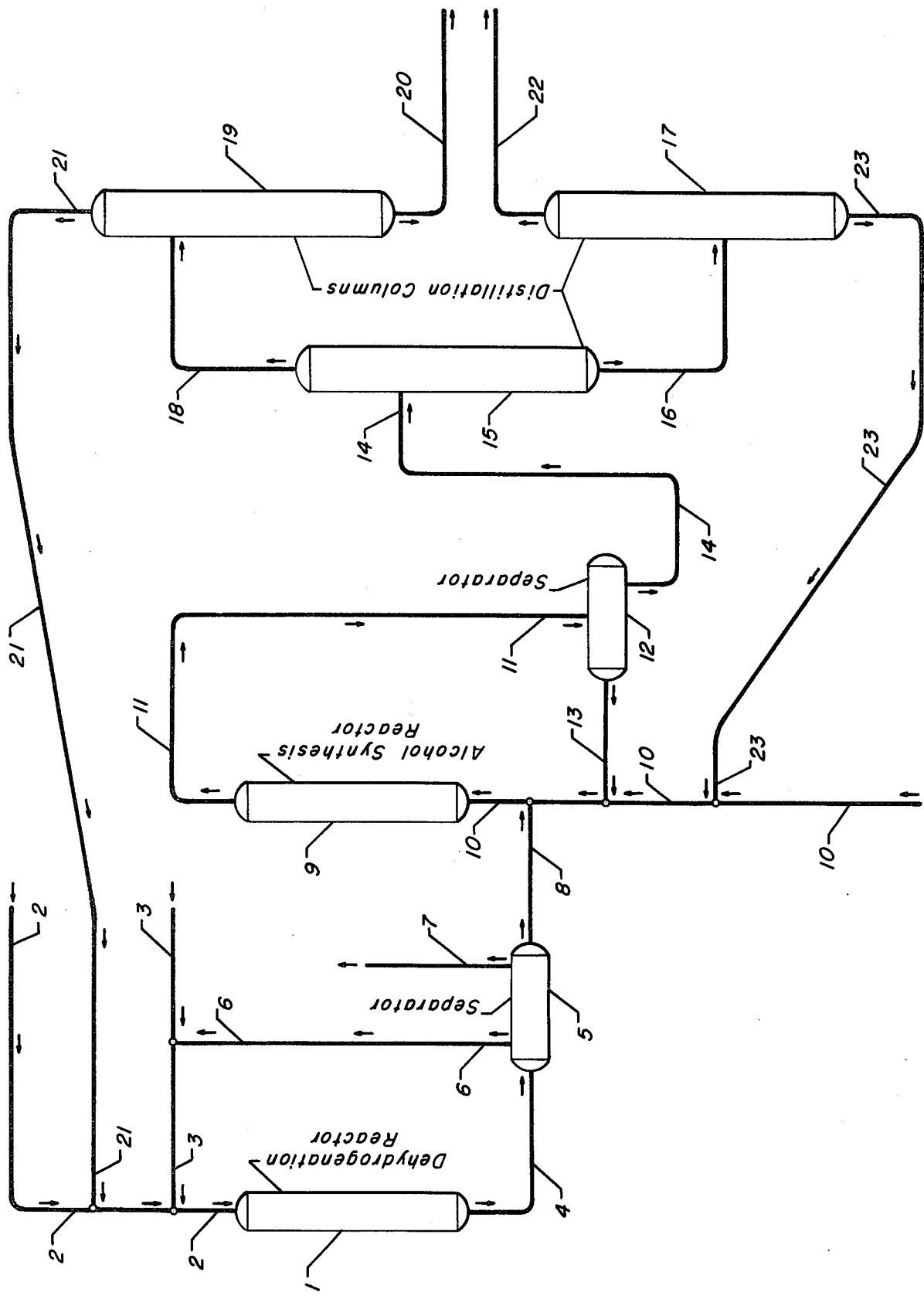

PREPARATION OF ALCOHOLS

CROSS-REFERENCE TO RELATED APPLICATIONS

This application is a continuation-in-part of my copending application Ser. No. 248,385 filed Mar. 27, 1981 and now abandoned which is a continuation-in-part application of copending application Ser. No. 93,461 filed Nov. 13, 1979 which is now abandoned, all teachings of which are incorporated herein by reference thereto.

BACKGROUND OF THE INVENTION

The hydration of olefins in a hydroformylation process to produce aldehydes or alcohols is known in the art. For example, Canadian Pat. No. 517,815 discloses that a charge comprising a mixture of olefins in which the olefins contain a different number of carbon atoms in the chain which were obtained by the cracking or dehydrogenation of a petroleum charge stock may be utilized as feed material for a hydroformylation reaction. The olefin mixture or olefin fractions from cracking or dehydrogenation processes are manufactured using hydrocarbon separation processes which are costly in nature. The patentee teaches that while alkanes may be present during the hydroformylation reaction, the removal of the alkane is taught when it is desired that the yield of alcohol is increased as evidenced by his statement that, if desired, the yield of alcohol may be increased somewhat by separating the liquid reaction products from any alkane which may be produced and thereafter hydrogenating the liquid products in a separate step under suitable conditions for the conversion of carbonyl and ester compounds to alcohol. As will hereinafter be shown in greater detail, this is in contradistinction to the process of the present invention whereby alkanes are not separated from the dehydrogenation effluent, but that the alcohol, which is produced according to the present reaction, is present to the substantial exclusion of the corresponding aldehyde. Likewise, another significant difference which is readily apparent between this patent and the instant invention is found in the fact that the patentee utilizes hydroformylation pressures in excess of 300 atmospheres to selectively prepare alcohols which again is in contradistinction to the process of the present invention which employs hydroformylation pressures of less than or up to 300 atmospheres. A further distinction between this patent and the present invention is found in the catalysts which are employed to effect the desired hydroformylation reaction. The hydroformylation catalyst which is utilized by the patentee includes nickel, cobalt, copper, and ruthenium carbonyl containing or mixed with chromium and/or cobalt. It is obvious from the patent that chromium and copper are the two essential and main ingredients of the hydroformylation catalyst which again differs from the hydroformylation catalyst of the present invention which utilizes a rhodium carbonyl compound in conjunction with a modifier such as a trialkyl-substituted monoamine. If so desired, the patentee further teaches that his catalyst may be used with other materials which serve as supports or promotors, these supports including such compounds as titania, silica, zirconia, kieselguhr, pumice and the like. Inherently, the process of this patent, in addition to producing alcohols, also produces aldehydes, esters and acids as by-products, the formation of such by-products with a subsequent separation step rendering the process economically less attractive to operate.

In addition to this patent, U.S. Pat. No. 3,912,785 teaches an Oxo reaction in which a specific feed is producing triethanolmethane and 3-methyl-1,5-pentanediol. However, the initial charge stock which is employed in this process is an admixture of two diols, namely, 3-methylene-1,5-pentanediol and 3-methyl-2-pentene-1,5-diol. The process described in this patent does not read upon the selective conversion of an admixture of an olefin and a paraffin to an alcohol as is the process of the present invention, but, alternatively, teaches the conversion of a mixture of diols to a diol in a trialkanol alkane. In like manner, U.S. Pat. No. 3,857,895 discloses a process for the hydroformylation of olefins employing, as a catalyst for the reaction, a Group VIII metal comprising an amidino or amino hydrocarbon ligand capable of forming a coordinate covalent bond with a metal atom and containing arsenic, antimony, phosphorus, or bismuth. The patentee discloses the viability use of a phosphorous compound in his process which is not at all operable in the process of the instant invention. However, the feedstock which is utilized for this reaction consists only of an olefinic charge stock and a mixture of dehydrogenation products which comprise the feedstock of the present process, although the patent teaches the use of organic solvents which may include aromatic hydrocarbons, alkyl or aryl ketones, ethers, esters, alcohols or aliphatic hydrocarbons. The mixture of olefins and solvents differs from the products formed by a dehydrogenation process. The latter, that is, the dehydrogenation products formed, may contain significant amounts of contaminants and/or by-products such as conjugated olefins, acetylene derivatives, trienes, and/or some aromatics. This is in contradistinction to the dehydrogenation products which are obtained by utilizing the process of the present invention which does not contain significant amounts of such undesirable contaminants and/or by-products.

U.S. Pat. No. 4,045,492 is drawn to a process for the manufacture of aldehydes and alcohols. This patent utilizes, as a catalyst for the reaction, a carbonyl complex of rhodium or cobalt plus a diaminodiphenylalkane as a modifying agent for the reaction. However, the feedstock for this process, as is the case of the previously discussed patents, consists only of an olefin, and results in the production of a predominately aldehyde product rather than a 100% selectivity for alcohol, which is the product of the present invention.

In addition to these prior art patents, U.S. Pat. No. 4,072,602 discloses a dehydrogenation process using an alumina-supported catalyst which consists of a platinum group metal, germanium, a Group VIB transition metal, alkali or alkaline earth metal and sulfur. The patentee, by utilizing a Group VIB transition metal component in the catalyst composite, produces a different dehydrogenation effluent inasmuch as the suitability of the quality of dehydrogenation products which are produced by the patented process is unpredictable. This unpredictability of the effluent is due to the presence of the Group VIB transition metal component plus a possible contamination of effluent product due to the presence of sulfur in the process. As will hereinafter be shown in greater detail, by utilizing a dehydrogenation catalyst of the type set forth in combination with a hydroformylation catalyst, it is possible to present a combined dehydrogenation-hydroformylation process to selectively produce alcohols without a further hydrogenation process to convert aldehydes into alcohols. The dehydrogenation catalysts which are employed in the present process constitute an important and essential factor to make the present process viable, inasmuch as the catalyst can produce a suitable dehydrogenation product which does not contain undesirable by-products or contaminants such as sulfur compounds which would be detrimental to the hydroformylation catalyst system which is employed in this process or which would make the recovery of the hydroformylation catalyst difficult to accomplish and thus, contributing to an added cost of operating the process.

As will hereinafter be shown in greater detail, I have now discovered a combined dehydrogenation-hydroformylation process in which an aliphatic feedstock can be subjected to dehydrogenation and the resultant dehydrogenation product comprising a mixture of aliphatic paraffinic hydrocarbons and aliphatic olefinic hydrocarbons can be subjected to a hydroformylation reaction without effecting a separation of the olefins and paraffins to selectively produce alcohols.

SUMMARY OF THE INVENTION

This invention relates to a process for the synthesis of alcohols. More specifically, the invention is concerned with a combination process for synthesizing alcohols in which a dehydrogenatable hydrocarbon is subjected to a dehydrogenation step in the presence of a nonacidic multimetallic catalyst. Thereafter, the product mixture which results from this step of the process is utilized, without a separation of the olefins resulting from the dehydrogenation process, as a feedstock for the alcohol synthesis step of the process.

In one aspect an embodiment of this invention resides in a process for the selective preparation of a hydroformylation product consisting essentially of an alcohol to the substantial exclusion of an aldehyde from a dehydrogenatable aliphatic, paraffinic hydrocarbon possessing from 2 to about 30 carbon atoms which comprises the steps of dehydrogenating said aliphatic paraffinhydrocarbon in a dehydrogenation zone in the presence of a non-acidic dehydrogenation catalyst consisting essentially of from about 0.01 to about 2.0 wt. % of a noble metal of Group VIII of the Periodic Table in the elemental metallic state, from about 0.1 to about 5.0 wt. % of at least one element selected from Groups IA and IIA of the Periodic Table present in an oxidation state and from about 0.01 to about 5.0 wt. % of at least one element selected from Groups IVA, VA and VIIB of the Periodic Table present in an oxidation state composited on a porous carrier material to produce a reaction product comprising vaporous light ends and a liquid dehydrogenation effluent mixture comprising both aliphatic olefinic hydrocarbons and aliphatic paraffinic hydrocarbons; transferring said vaporous light ends and said liquid dehydrogenation products to a gas-liquid separation zone; separating said vaporous light ends from said liquid dehydrogenation effluent mixture comprising both aliphatic olefinic and aliphatic paraffinic hydrocarbons; passing said liquid dehydrogenation effluent mixture without any separation of said aliphatic olefinic hydrocarbon from aliphatic paraffinic hydrocarbon to a hydroformylation zone; hydroformylating said liquid dehydrogenation effluent mixture at hydroformylation conditions which include a temperature in the range of from about 50° to about 350° C. and a pressure in the range of from about 10 up to less than 300 atmospheres by treating said mixture with carbon monoxide and hydrogen in the presence of both a hydroformylation catalyst consisting essentially of a rhodium carbonyl compound and a promotor comprising a trialkyl-substituted amine in which all three of said alkyl moieties are substituted to the nitrogen atom of said amine; and recovering the selectively produced alcohol.

A specific embodiment of this invention is found in the process for the selective preparation of an alcohol from a dehydrogenatable aliphatic paraffinic hydrocarbon which comprises dehydrogenating n-heptane in a dehydrogenating zone in the presence of a catalyst comprising platinum, tin and lithium composited on alumina at a temperature in the range of from about 400° to about 700° C. and a pressure in the range of from about 0.1 to about 10 atmospheres to produce a reaction product comprising vaporous light ends and a liquid dehydrogenation effluent comprising n-heptane and n-heptene, transferring the vaporous light ends and liquid dehydrogenation products to a gas-liquid separation zone, separating the vaporous light ends from the n-heptane and n-heptene, passing the mixture of n-heptane and n-heptene to a hydroformylation zone, hydroformylating said mixture at a temperature in the range of from about 50° to about 350° C. and a pressure in the range of from about 10 to about 300 atmospheres by treating the mixture with carbon monoxide and hydrogen in the presence of a catalyst comprising chlorodicarbonylrhodiumdimer and a promoter comprising N,N,N-dimethyldodecylamine, and recovering the desired octyl alcohol.

Other objects and embodiments will be found in the following further detailed description of the present invention.

DETAILED DESCRIPTION OF THE INVENTION

As hereinbefore set forth, the present invention is concerned with a process for synthesizing alcohols by utilizing a combination process in which a product mixture which results from the dehydrogenation of dehydrogenatable materials may be utilized as a feedstock for a subsequent hydroformylation reaction involving the treatment of the resulting dehydrogenated product mixture with carbon monoxide and hydrogen in the presence of certain catalytic compositions of matter. The dehydrogenatable product mixture comprises a mixture of aliphatic paraffinic hydrocarbons and aliphatic olefinic hydrocarbons. It is used in the hydroformylation reaction without a separation of the dehydrogenated hydrocarbons from the unconverted hydrocarbons. The olefins which are present in the product mixture are selectively converted into alcohols in a one-step process which is unlike the conversion of olefins into predominately aldehyde products which is found in prior processes. In this respect, it was unexpected that by utilizing the present process, it was possible to obtain an approximately 100% selectivity for alcohols with a corresponding 100% conversion of olefins from the product mixture resulting from a prior dehydrogenation step without separating the components of the product mixture. This is in contradistinction to prior reactions involving an Oxo process which did not result in the production of predominately alcoholic products at approximately 100% yield, but produced a mixture of product which included alcohols, aldehydes, esters and acids.

The dehydrogenation of the dehydrogenatable hydrocarbons is effected by contacting said hydrocarbons at dehydrogenation conditions with a nonacidic catalytic composite of a type hereinafter set forth in greater detail. Dehydrogenatable hydrocarbons which are utilized in the present process preferably comprise paraffinic hydrocarbons containing from about 2 to about 30 carbon atoms per molecule such as normal aliphatic hydrocarbons or cycloaliphatic hydrocarbons containing from about 4 to about 10 carbon atoms. The organic compound which is to undergo dehydrogenation will be capable of being dehydrogenated to produce products containing the same number of carbon atoms, but fewer hydrogen atoms, and which are capable of being vaporized at the dehydrogenation conditions which are utilized in the particular step of the process. Some specific examples of suitable dehydrogenatable hydrocarbons will include the aliphatic paraffins such as ethane, propane, n-butane, isobutane, n-pentane, iso-pentane, n-hexane, 2-methylpentane, 2,2-dimethylbutane, n-heptane, 2-methylhexane, 2,2-dimethylpentane, the isomeric octanes, nonanes, decanes, undecanes, dodecanes, tridecanes, tetradecanes, pentadecanes, hexadecanes, heptadecanes, octadecanes, nonadecanes, eicosanes, heneicosanes, docosanes, tricosanes, tetracosanes, pentacosanes, hexacosanes, heptacosanes, octacosanes, nonacosanes, triacontanes, etc., naphthenes such as cyclobutane, cyclopentane, cyclohexane, methylcyclopentane, cycloheptane, ethylcyclopentane, methylcyclohexane, cyclooctane, 1,3-dimethylcyclohexane, isopropylcyclopentane, methylcycloheptane, etc. While the feedstream of the dehydrogenatable hydrocarbon may comprise one particular paraffinic or cycloparaffinic hydrocarbon, it is also contemplated that the feedstream may contain a mixture of 4 or 5 adjacent normal paraffin homologues such as $C_{10}$–$C_{13}$, $C_{11}$–$C_{14}$, $C_{11}$–$C_{15}$ and the like mixtures.

The dehydrogenation of the aforementioned dehydrogenatable hydrocarbons is effected in the presence of a nonacidic catalyst composite which contains a Group VIII noble metal and at least one element selected from Group IA and IIA metals and at least one element selected from Group IVA, VA and VIIB metals of the Periodic Table composited on a porous carrier material. These nonacidic multimetallic catalytic composites will possess improved activity, selectivity and stability characteristics. Examples of noble metals of Group VIII of the Periodic Table which comprise one component of the catalyst composite will preferably include platinum, palladium, iridium, etc. Examples of Group IA and IIA of the Periodic Table will include lithium, sodium, potassium, rubidium, cesium, magnesium, calcium, strontium, while elements of Groups IVA, VA and VIIB which may be employed will include in particular germanium, tin, lead, arsenic, antimony, bismuth and rhenium. In a preferred embodiment, the nonacidic catalytic composite will contain on an elemental basis about 0.01 to about 2 wt. % of the noble metal of Group VIII, from about 0.01 to about 5 wt. % of the alkali or alkaline earth metal, and from about 0.01 to about 5 wt. % of the Group IVA, VA and VIIB elements, said components being uniformly dispersed throughout the porous carrier material, wherein substantially all of the noble metal components are present in the corresponding elemental metallic states and wherein substantially all of the Group IVA, VA and VIIB component and the alkali or alkaline earth metal component are present in an oxidation state above that of the elemental metal.

As hereinbefore set forth, the multimetallic components are composited on a porous carrier material. It is preferred that this material be a porous, adsorptive, high surface area support having a surface area of about 25 to about 500 $m^2/g$. The porous carrier material should be relatively refractory to the conditions utilized in the dehydrogenation process, and it is intended to include within the scope of the present invention carrier materials which have traditionally been utilized in hydrocarbon conversion catalysts such as : (1) activated carbon, coke or charcoal; (2) silica or silica gel, silicon carbide, clays and silicates including those synthetically prepared and naturally occurring, which may or may not be acid-treated, for example, attapulgus clay, china clay, diatomaceous earth, fuller's earth, kaolin, kieselguhr, etc.; (3) ceramics, porcelain, crushed firebrick, bauxite; (4) refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, etc.; (5) crystalline zeolitic aluminosilicates such as naturally occurring or synthetically prepared mordenite and/or faujasite, either in the hydrogen form or in a form which has been treated with multivalent cations; and (6) combination of elements from one or more of these groups. The preferred porous carrier materials for use in the present invention are refractory inorganic oxides, with best results obtained with an alumina carrier material. Suitable alumina materials are the crystalline aluminas known as the gamma-, eta- and theta-aluminas, with gamma-alumina giving best results. In addition, in some embodiments, the alumina carrier material may contain minor proportions of other well-known refractory inorganic oxides such as silica, zirconia, magnesia, etc.; however, the preferred support is substantially pure gamma-alumina. Preferred carrier materials have an Apparent Bulk Density of about 0.2 to about 0.8 g/cc and surface area characteristics such that the average micropore diameter measured by nitrogen adsorption is about 20 to 300 Angstroms, the pore volume is about 0.1 to 1 cc/g and the surface area is about 10 to about 500 $m^2/g$. In general, excellent results are typically obtained with a gamma-alumina carrier material which is used in the form of spherical particles having: a relatively small diameter (i.e. typically about 1/16 inch), an Apparent Bulk Density of about 0.3 g/cc, a pore volume of about 0.5 cc/g and a surface area of about 170 $m^2/g$.

The preferred alumina carrier material may be prepared in any suitable manner, and may be prepared in a synthetic manner or may be naturally occurring. However, the alumina to be employed may be activated prior to use by one or more treatments including drying, calcination, steaming, etc. For example, the alumina carrier may be prepared by adding a suitable alkaline reagent, such as ammonium hydroxide, to a salt of alumina such as aluminum chloride in such an amount as to form an aluminum hydroxide gel which, upon drying or calcining, is converted to alumina. The alumina carrier may be formed in any desired shape such as spheres, pills, cakes, extrudates, powders, granules, etc. A particularly preferred form of alumina is the sphere, and these spheres may be continuously manufactured by the well-known oil drop method which comprises the steps of: (1) forming an alumina hydrosol by any of the techniques taught in the art and preferably by reacting alumina metal with hydrochloric acid; (2) combining the resulting hydrosol with a suitable gelling agent; and (3) dropping the resultant mixture into an oil bath which is maintained at elevated temperatures. The droplets of the mixture remain in the oil bath until they set and form spheres, said spheres then being continuously withdrawn from the oil bath and typically subjected to specific aging treatments in oil and an ammoniacal solution to further improve their physical characteristics. The resulting aged and gelled particles are then washed and dried at a relatively low temperature of from about 300° to about 400° F. followed by a calcination procedure at a temperature of about 850° to about 1300° F. for a period of from about 1 to about 20 hours.

One component of the multimetallic catalyst comprises an element of Group IVA, VA and VIIB of the Periodic Table such as germanium, tin, arsenic, antimony, bismuth, rhenium, or lead. Substantially all of the Group IVA, VA and VIIB elements will be present in the final catalyst in an oxidation state above that of the elemental metal. This component may be present in chemical combination with one or more of the other ingredients of the composite, or as a chemical compound of germanium, tin or lead such as the oxide, sulfide, halide, oxyhalide, oxychloride, aluminate, etc. compounds, the preferred form of the compound being that of the corresponding oxide. This component is preferably present in the final composite in an amount in the range of from about 0.01 to about 5 wt. % thereof, calculated on an elemental basis, the most preferred amount being from about 0.05 to about 2 wt. %. This component may be incorporated in the composite in any suitable manner known in the art, the end result being in a uniform dispersion of the moiety throughout the carrier material, such as coprecipitation or cogelation with the porous carrier material, ion exchange with the carrier material or impregnation of the carrier material at any stage in its preparation. For example, one method of incorporating this component into the composite involves the utilization of a soluble decomposable compound of the Group IVA metal to impregnate the porous carrier material either before, during or after the carrier material is calcined. The solvent which is used during this impregnation step is selected on the basis of its capability to dissolve the desired compound without effecting the porous carrier material which is to be impregnated, good results being obtained when water is the solvent and thus the preferred compound for use in this impregnation step is typically water-soluble and decomposable. Regardless of which impregnation solution is utilized, the component may be impregnated either prior to, simultaneously with, or after the other metallic components are added to the carrier material.

A second metallic component of the multimetallic catalytic composite includes a noble metal of Group VIII of the Periodic Table such as platinum, palladium, ruthenium, rhodium, osmium or iridium. This component will generally comprise about 0.01 to about 2 wt. % of the final catalytic composite calculated on an elemental basis and the noble metal will exist within the final catalytic composite in the elemental metallic state. This component may also be incorporated in the catalytic composite in any suitable method known to result in a relatively uniform distribution of this component in the carrier material, said methods including coprecipitation, cogelation, ion exchange or impregnation. Again, as in the case of the Group IVA metal component of the catalyst, one method of preparing the composite involves the utilzation of a soluble, decomposable compound to impregnate the carrier material in a relatively uniform manner. For example, as an illustration thereof, this component may be added to the support by commingling said support with an aqueous solution of chloroplatinic or chloropalladic acid. Another method for incorporating this component into the catalytic composite comprises cogelling or coprecipitating the components such as iridium during the preparation of the carrier material. This is accomplished by the use of a soluble, decomposable compound of iridium such as chloroiridic acid or iridium tetrachloride to the alumina hydrosol before it is gelled. Thereafter, the resulting mixture is then finished by conventional gelling, aging, drying and calcination steps.

Another component of the multimetallic catalytic composite which is utilized to dehydrogenate a dehydrogenatable hydrocarbon is a compound of Groups IA or IIA of the Periodic Table, that is, an alkali or alkaline earth component. In the preferred embodiment, this component is selected from the groups consisting of compounds of the alkali metals, namely cesium, rubidium, potassium, sodium and lithium and of the alkaline earth metals, namely, calcium, strontium, barium and magnesium. This component exists within the catalytic composite in an oxidation state above that of the elemental metal such as a relatively stable compound including the oxide or sulfide, or in combination with one or more of the other components of the composite, or in combination with the carrier material such as, for example, in the form of a metal aluminate. The amount of this component is preferably selected to provide a nonacidic composite containing from about 0.1 to about 5 wt. % of the alkali or alkaline earth metal, and more preferably, from about 0.25 to about 3.5 wt. %. In the preferred embodiment, this component of the multimetallic catalyst composite will be a compound of lithium or potassium. The function of this component is to neutralize any of the acidic material which may have been used in the preparation of the catalyst in order to insure that the final catalyst composite is nonacidic in nature. Again, as in the case of the previously mentioned metallic components of the catalyst composite, the alkali or alkaline earth component may be combined with the porous carrier material in any manner known to those skilled in the art in order to result in a relatively uniform dispersion of this component throughout the carrier material with a subsequent neutralization of any acidic sites which may be present thereon. Best results are ordinarily obtained when this component is added to the carrier material in a step subsequent to the addition of the other metallic components inasmuch as the alkali metal or alkaline earth metal acts to neutralize the acid used in the preferred impregnation procedure for these metallic components. For example, the Group VIII noble metal component and the Group IVA metal component may be added to the carrier material and the resulting composite oxidized in a stream of air at a high temperature in the range of from about 600° to about 1000° F. following which the resulting oxidized component may be treated with steam or a mixture of air and steam in order to remove at least a portion of any residual acidity, and thereafter add the alkali metal or alkaline earth metal component.

In the preferred embodiment of the invention, the dehydrogenation catalyst will comprise a mixture of platinum-tin-lithium composited on an alumina support, platinum-germanium-lithium composited on an alumina support, etc.

In the process of the present invention, the dehydrogenatable hydrocarbon is contacted with a non-acidic multimetallic catalytic composite of the type hereinbefore set forth in greater detail in a dehydrogenation zone at dehydrogenating conditions. The contact of the hydrocarbon with the catalytic composite may be accomplished by using the catalyst in a fixed bed system, a moving bed system, a fluidized bed system or in a batch-type operation. In the preferred embodiment the catalyst is disposed as a fixed bed in a dehydrogenation zone and a hydrocarbon feed stream which has been preheated by any suitable means to the desired reaction temperature is passed into said zone. It is, of course, understood that the dehydrogenation zone may be one or more separate reactors with suitable heating means therebetween to insure that the desired conversion temperature is maintained at the entrance to each reactor. The reactants may be contacted with the catalyst bed in either an upward, downward or radial flow phase and may be in the liquid phase, a mixed liquid-vapor phase or a vapor phase when in contact with the catalyst, the best results being obtained when utilizing a vapor phase reaction.

Although hydrogen is the preferred diluent for us in the reaction, it is also contemplated within the scope of this invention that other art-recognized diluents such as steam, methane, carbon dioxide and the like may also be advantageously utilized. In the preferred embodiment of the invention, hydrogen is utilized due to the fact that it serves the dual function of not only lowering the partial pressure of the dehydrogenatable hydrocarbon, but also suppressing the formation of hydrogen-deficient, carbonaceous deposits on the catalytic composite. Ordinarily, hydrogen is utilized in amounts sufficient to insure a hydrogen to hydrocarbon mole ratio of about 1:1 to about 20:1, with best results obtained in the range of from about 1.5:1 to about 10:1. The hydrogen stream which is charged to the dehydrogenation zone will typically comprise recycled hydrogen which has been obtained from the effluent stream from the dehydrogenation zone after a suitable separation step. In addition, when hydrogen is used as the diluent, it is also contemplated that water or a water-producing compound be added to the dehydrogenation zone. This water additive may be included in the charge stock or in the hydrogen stream, or in both of these, or added independently. Ordinarily, it is preferred to inject the necessary water by saturating at least a portion of the input hydrogen stream with water. The amount of equivalent water which is added to the reaction zone should be of sufficient quantity to maintain the total amount of water continuously entering the dehydrogenation zone in a range of from about 50 to about 10,000 weight ppm of the charge stock.

The reaction conditions or dehydrogenation conditions which are utilized are those which are generally selected from the conditions well known to those skilled in the art for the particular dehydrogenatable hydrocarbon which is charged to the zone. More specifically, suitable conversion temperatures are selected from the range of from about 400° C. to about 700° C., the particular temperature being dependent upon the dehydrogenatable hydrocarbon which comprises the feedstock. For example, temperatures within the lower portion of the range will be employed when subjecting the more easily dehydrogenated hydrocarbons such as long chain normal paraffins and from the higher portion of the range when subjecting the more difficultly dehydrogenated hydrocarbons to the process. In addition, the pressure which is utilized for the employment of this dehydrogenation process is ordinarily selected at a value which is as low as possible and yet consistent with the maintenance of catalyst stability. This pressure is usually in the range of from about 0.1 to about 10 atmospheres. The effluent stream which is recovered from the dehydrogenation zone will contain unconverted dehydrogenatable hydrocarbons as well as products of the dehydrogenation reaction and will, after being subjected to a cooling step, be passed into a second zone, without separating the unconverted hydrocarbons from the dehydrogenated hydrocarbons to a second zone wherein the synthesis of alcohols is effected. In this zone, the product mixture will be contacted with carbon monoxide and hydrogen in the presence of certain catalytic compositions of matter comprising rhodium- or ruthenium-containing compounds which are modified by the additional presence of a tertiary amine compound.

The reaction conditions which are employed for effecting the selectivity of alcohols will include a temperature of from about 50° to about 350° C. and a pressure which will be in the range of from about 10 up to less than about 300 atmospheres. In the preferred embodiment of the invention, the pressures which are employed will be at autogenous pressures resulting from the presence of carbon monoxide and hydrogen in the reaction mixture, although it is also contemplated within the scope of this invention that the pressures resulting from the use of carbon monoxide and hydrogen will comprise only a partial operating pressure, the remainder of the desired pressure being afforded by the introduction of the substantially inert gas such as nitrogen, helium, argon, etc. into the reaction vessel. Other reaction conditions for the synthesis of alcohols will include mole ratios of the various components. For example, the molar ratio of olefin to the rhodium which is present in the catalytic composition of matter will be in a range of from about 300 to about 3000 moles of olefin per mole of metal. Likewise, the molar ratio of tertiary amine to rhodium is in a range of from about 30 to about 300 moles of tertiary amine per mole of metal. Examples of rhodium-containing compounds which provide the catalyst of the present invention will be selected from the carbonyl and hydrocarbonyl complexes of the metal as well as from nitrates or hydrides of rhodium which will form carbonyl complexes under the reaction conditions which are employed for the process. Specific examples of these compounds will include rhodium nitrate, rhodium chloride, rhodium bromide, rhodium iodide, rhodium fluoride, chlorodicarbonylrhodiumdimer, rhodium carbonyl, chlorobis(ethylene)rhodiumdimer, hexarhodiumhexadecacarbonyl, tetrarhodiumundodecacarbonyl, etc. Organorhodium complexes having an organophosphine ligand are excluded as catalysts since a phosphine ligand suppresses alcohol selectivity. It is to be understood that the aforementioned rhodium-containing compounds are only representative of the class of compounds which may be employed, and that the present invention is not necessarily limited thereto.

In addition, the hydroformylation reaction is also effected in the presence of a promoter comprising a tertiary amine which acts as a promoter for the catalyst, thus enabling the hydroformylation of the aliphatic olefinic hydrocarbons in the dehydrogenation product mix to be selectively hydroformylated to an alcohol. Some specific examples of the type of tertiary amines comprising a trialkyl-substituted monoamine, all three of said alkyl moieties being substituted to the nitrogen of the amine, will include dimethylpropylamine, dimethylbutylamine, dimethylpentylamine, dimethylhexylamine, dimethylheptylamine, dimethyloctylamine, dimethyldecylamine, dimethyldodecylamine, dimethylpentadecylamine, dimethyleicosylamine, dimethyldocosylamine, diethylpropylamine, diethyloctylamine, diethylundecylamine, dipropylhexylamine, dipropylnonylamine, dipropylheptadecylamine, tributylamine, dibutylpentylamine, dibutyloctylamine, etc.

It is to be understood that the aforementioned trialkyl-substituted monoamines are only representative of the class of compounds which may be used, and that the present invention is not necessarily limited thereto.

BRIEF DESCRIPTION OF THE DRAWING

The present invention will be further illustrated with reference to the accompanying drawing which sets forth an illustrative flow diagram of one embodiment of the process of this invention. It is to be understood that various valves, pumps, etc. have been eliminated as not being essential to the complete understanding of the present invention. However, the utilization of these as well as other similar appurtenances will become obvious as the drawing is described. Referring now to the drawing, a charge stock comprising a dehydrogenatable hydrocarbon or a mixture of dehydrogenatable hydrocarbons such as paraffins is charged to dehydrogenation reactor 1 through line 2. Dehydrogenation zone 1 contains a catalyst of the type hereinbefore set forth in greater detail, the catalyst preferably being positioned in reactor 1 in the form of a fixed bed. In addition, a stream of hydrogen may also be charged to dehydrogenation reactor 1 through line 3. In dehydrogenation reactor 1, the dehydrogenatable hydrocarbons are contacted with the catalyst at dehydrogenation conditions which include a temperature in the range of from about 400° to about 700° C. and a pressure in the range of from about 0.1 to about 10 atmospheres, the reaction parameters being dependent upon the particular hydrocarbon which is to undergo dehydrogenation. After passage through dehydrogenation reactor 1, the effluent is withdrawn through line 4 and passed to gas/liquid separator 5, the light products comprising hydrogen and vaporous light ends are separated from the liquid dehydrogenation effluent mixture comprising aliphatic paraffinic hydrocarbons and aliphatic olefinic hydrocarbons. The light products comprising hydrogen and vaporous light ends are withdrawn through line 6 and partly recycled back to dehydrogenation reactor 1 in admixture with the added hydrogen through lines 3 and 2. Any light vaporous products which may have been formed during the dehydrogenation reaction as by-products are withdrawn from separator 5 through vent line 7. The dehydrogenation product mixture comprising the aliphatic paraffinic hydrocarbons and aliphatic olefinic hydrocarbons is withdrawn from gas/liquid separator 5 through line 8. This reactor also contains a catalyst of the type hereinbefore set forth, that is, a rhodium-containing compound which is fed to reactor 9 through line 10 in the form of a homogeneous catalyst. In synthesis reactor 9, the product mixture is contacted with a mixture of carbon monoxide and hydrogen along with a trialkyl-substituted monoamine in which all alkyl substituents are substituted on the nitrogen atom of the amine modifier which is charged to reactor 9 through line 10 In alcohol synthesis reactor 9, which is maintained at the reaction conditions which include a temperature in the range of from about 50° to about 350° C. and a pressure in the range of from about 10 to about 300 atmospheres, the synthesis of the alcohol will occur. The effluent from reactor 9 is withdrawn through line 11 and passed to second gas/liquid separator 12 wherein any unreacted carbon monoxide and hydrogen are separated from the liquid and recycled back to reactor 9 through line 13. The liquid effluent comprising the reaction mixture containing paraffins, unreacted olefins, alcohols, the trialkyl-substituted monoamine modifier, and the catalyst are withdrawn from separator 12 through line 14 and passed to a first distillation column 15. In distillation column 15, the alcohols which comprise the desired product of the process along with any catalyst complex which may have also been removed from alcohol synthesis reactor 9 are withdrawn through line 16 and passed to a second distillation column 17. The unreacted dehydrogenatable hydrocarbons are withdrawn from first distillation column 15 through line 18 and passed to a third distillation column 19 wherein the aforesaid dehydrogenatable compounds are separated from any heavies or bottoms which are withdrawn through line 20 for removal. The dehydrogenatable hydrocarbons are withdrawn from distillation column 19 through line 21 and recycled back to line 2 to act as a portion of the feedstock which is charged to dehydrogenation reactor 1. In distillation column 17, the alcohols which comprise the desired products of this process are separated from any catalyst and withdrawn from distillation column 17 through line 22 and passed to storage. The catalyst complex which has been separated from the alcohols is withdrawn from distillation column 17 through line 23 and recycled through line 23 back to alcohol synthesis reactor 9 through line 10.

It is to be understood, of course, that variations and modifications may be made to the illustrated flow scheme without necessarily departing from the scope of this invention. For example, it is also contemplated within the scope of this invention that another embodiment involves the separation of the alcohol synthesis catalyst comprising the rhodium-containing compound from the effluent withdrawn from separator 12. If this embodiment is to be effected, the catalyst is separated from the effluent by extraction with an appropriate aqueous solvent in an extraction column which is not shown in the drawing, but may be located on line 14. Following this, the catalyst-free organic raffinate is separated by distillation in subsequent consecutive steps involving distillation columns 15, 17, and 19 while the concentrated catalyst solution may then be recycled to alcohol synthesis reactor 9.

Examples of alcohols which may be prepared according to the process of this invention will include propyl alcohol, the isomeric butyl alcohols, pentyl alcohols, hexyl alcohols, heptyl alcohols, octyl alcohols, nonyl alcohols, decyl alcohols, undecyl alcohols, dodecyl alcohols, tridecyl alcohols, tetradecyl alcohols, pentadecyl alcohols, hexadecyl alcohols, heptadecyl alcohols, octadecyl alcohols, nonadecyl alcohols, eicosyl alcohols, heneicosyl alcohols, docosyl alcohols, tricosyl alcohols, tetracosyl alcohols, pentacosyl alcohols, hexacosyl alcohols, heptacosyl alcohols, octacosyl alcohols, nonacosyl alcohols, triacontyl alcohols, hentriacontyl alcohols, etc.

The following examples are given for purposes of illustrating the process of this invention. However, it is to be understood that these examples are merely illustrative in nature and that the present process is not necessarily limited thereto.

EXAMPLE I

A reactor was loaded with 1 to 2 grams of a 16-20 mesh nonacidic catalyst containing 0.364 wt. % platinum, 0.52 wt. % tin, and 0.55 wt. % lithium supported on an alumina base, said alumina having an Apparent Bulk Density of 0.3 g/cc. A feed stream comprising n-heptane was contacted with the catalyst at a temperature in the range of from about 520° to 525° C., a pressure ranging from 15 to 25 psig at a Liquid Hourly Space Velocity of about 50 hrs.$^{-1}$. In addition, hydrogen was also passed to the reactor at a rate of 8 moles of hydrogen per mole of n-heptane.

The hydrocarbon product stream from this reactor which consisted of 83.85 wt. % n-heptane, 14.05 wt. % of n-heptene along with minor amounts of isoheptane, isoheptene, isoheptadiene, dimethylcyclopentane, and toluene was charged to an 850 cc autoclave containing 1.10 grams of dimethyldodecylamine and 0.0095 gram of a catalyst comprising chlorodicarbonylrhodiumdimer. The 31.24 grams of the product mix along with the modifier and catalyst were sealed into the autoclave and a blend gas consisting of a 1:1 mole ratio of carbon monoxide to hydrogen was charged to the autoclave until an initial operating pressure of 150 atmospheres was reached. The autoclave was then heated to a temperature of 150° C. and maintained thereat for a period of 3 hours, the pressure in the autoclave during this period dropping from 201 to 199 atmospheres. During the reaction period, the molar ratio of olefin to catalyst was 979:1 and the molar ratio of modifier to catalyst was 113:1. At the end of the residence time, heating was discontinued and the autoclave was allowed to return to room temperature. Upon reaching room temperature, the excess pressure was discharged and the reaction mixture was recovered therefrom. Analysis of the product by means of gas-liquid chromatography analysis disclosed that there had been a 100% conversion of the olefins with a 93.0% selectivity to n-octyl alcohol, the remaining selectivity, namely 7%, being to octanal.

EXAMPLE II

In a manner similar to that set forth in Example I above, a charge of n-heptane was treated in the presence of hydrogen and a catalyst similar in nature to that hereinbefore set forth under identical operating conditions of temperature, pressure, Liquid Hourly Space Velocity and hydrogen to heptane feed ratio. The product mix (30.76 grams) resulting from this treatment was then charged to an 850 cc rotating autoclave which contained 1.72 grams of dimethydodecylamine and 0.0113 gram of chlorodicarbonylrhodiumdimer. The autoclave was again sealed and a blend gas comprising a 1:1 ratio of carbon monoxide to hydrogen was charged thereto until an initial operating pressure of 850 atmospheres was reached. The autoclave was then heated to a temperature of 150° C. and maintained thereat for a period of 3 hours, the pressure in said autoclave rising from 195 atmospheres to 202 atmospheres. In this instance, the molar ratio of olefin to catalyst was 810:1 and the molar ratio of modifier to catalyst was 148:1. At the end of the reaction time, heating was discontinued and the autoclave was allowed to return to room temperature. Upon reaching room temperature, the excess pressure was discharged and the reaction mixture was recovered therefrom. Analysis of the product by means of gas-liquid chromatography analysis disclosed that there had been a 100% conversion of the olefin with a 100% conversion to octyl alcohol.

EXAMPLE III

A reactor containing 5.56 grams of a catalyst similar in nature to that set forth in Example I above was contacted with a paraffinic hydrocarbon containing a mixture of from $C_{11}$ to $C_{14}$ normal paraffins. The feed stream was contacted with the catalyst at a temperature of 475° C., a pressure of 30 psig, and a Liquid Hourly Space Velocity of 32 hrs.$^{-1}$. In addition, hydrogen was also charged to the reactor at a rate sufficient to maintain a normal ratio of 8 moles of hydrogen per mole of paraffin. The dehydrogenation product stream which comprised a mixture of normal aliphatic paraffinic hydrocarbons and normal aliphatic olefinic hydrocarbons was recovered from the reactor and 29.17 grams of this product mixture were charged to an 850 cc autoclave along with 4.75 grams of dimethyldodecylamine and 0.0333 gram of chlorodicarbonylrhodiumdimer. After sealing the autoclave and charging a 1:1 mole ratio of carbon monoxide to hydrogen blend gas until an initial pressure of 150 atmospheres was reached, the autoclave was then heated to a temperature of 150° C. After allowing the synthesis process to proceed for a period of 3 hours during which time the operating pressure varied from 198 to 197 atmospheres, heating was discontinued and the autoclave allowed to return to room temperature. The excess pressure was discharged and the reaction product, after recovery therefrom was subjected to gas-liquid chromatography analysis. This analysis showed that there had been a greater than 99% conversion of the olefins with a 100% mole selectivity to alcohols ranging from dodecyl alcohol to pentadecyl alcohol.

A repeat of the above experiment under similar conditions using similar catalysts, modifier, and feedstream resulted in a 99% conversion of the olefins with a 72.5% selectivity to alcohols. As in the above experiment, the alkyl portion of the oxygenated product ranged from dodecyl to pentadecyl in length. It is therefore readily apparent that by utilizing the process of the present invention in which the product mix from the dehydrogenation of aliphatic paraffinic hydrocarbons, that is, a mixture of these aliphatic paraffinic hydrocarbons and the corresponding aliphatic olefinic hydrocarbons may be subjected to a hydroformylation reaction in the presence of a rhodium-containing catalyst and a trialkyl-substituted monoamine in which the three alkyl moieties are all substituted on the nitrogen atom of the amine, will result in the obtention of a major portion of the desired alcohols, the selectivity of said process to alcohol ranging 100% in some instances and averaging well above 85-90%.

EXAMPLE IV

When various other aliphatic paraffinic hydrocarbons such as isobutane, pentane, etc. are contacted in a dehydrogenation zone with a dehydrogenation catalyst comprising platinum, germanium and lithium composited on alumina, the dehydrogenation product mix, without separation of the resulting aliphatic olefinic hydrocarbons from the original aliphatic paraffinic hydrocarbons, may be treated in a hydroformylation zone with carbon monoxide and hydrogen in the presence of a hydroformylation catalyst comprising rhodium carbonyl and a trialkyl substituent monoamine such as N,N,N-trimethylamine to form the corresponding pentyl and hexyl alcohols.

I claim as my invention:

1. A process for the selective preparation of an alcohol hydroformylation product to the substantial exclusion of an aldehyde from a dehydrogenatable aliphatic paraffinic hydrocarbon possessing from 2 to about 30 carbon atoms which comprises the steps of:
   (a) dehydrogenating said aliphatic paraffinic hydrocarbon in a dehydrogenation zone in the presence of from about 0.01 to about 2.0 wt. % of a noble metal of Group VIII of the Periodic Table in the elemental metallic state, from about 0.1 to about 5.0 wt. % of at least one element selected from Groups IA and IIA of the Periodic Table present in an oxidation state and from about 0.01 to about 5.0 wt. % of at least one element selected from Groups IVA, VA and VIIB of the Periodic Table present in an oxidation state composited on a porous alumina or silica carrier material to produce a reaction product comprising vaporous light ends and a liquid dehydrogenation effluent mixture comprising both aliphatic olefinic hydrocarbons and aliphatic paraffinic hydrocarbons;
   (b) transferring said vaporous light ends and said liquid dehydrogenation products to a gas-liquid separation zone;
   (c) separating said vaporous light ends from said liquid dehydrogenation effluent mixture comprising both aliphatic olefinic and aliphatic paraffinic hydrocarbons;
   (d) passing said liquid dehydrogenation effluent mixture without any separation of said aliphatic olefinic hydrocarbon from aliphatic paraffinic hydrocarbon to a hydroformylation zone;
   (e) hydroformylating said liquid dehydrogenation effluent mixture at hydroformylation conditions which include a temperature in the range of from about 50 to about 350° C. and a pressure in the range of from about 10 up to less than 300 atmospheres by treating said mixture with carbon monoxide and hydrogen in the presence of both a hydroformylation catalyst consisting essentially of a rhodium carbonyl compound and a promoter comprising a trialkyl-substituted amine in which all three of said alkyl moieties are substituted to the nitrogen atom of said amine; and
   (f) recovering the selectively produced alcohol.

2. The process as set forth in claim 1 in which said dehydrogenation conditions include a temperature in the range of from about 400° to about 700° C. and a pressure in the range of from about 0.1 to about 10 atmospheres.

3. The process as set forth in claim 1 in which said hydroformylation catalyst is chlorodicarbonylrhodium-dimer.

4. The process as set forth in claim 1 in which said hydroformylation catalyst is rhodium carbonyl.

5. The process as set forth in claim 1 in which said trialkyl-substituted amine is N,N,N-dimethyldodecylamine.

6. The process as set forth in claim 1 in which said trialkyl-substituted amine is N,N,N-trimethylamine.

7. The process as set forth in claim 1 in which said dehydrogenatable aliphatic paraffinic hydrocarbon is n-heptane and said alcohol is octyl alcohol.

8. The process as set forth in claim 1 in which said dehydrogenatable aliphatic paraffinic hydrocarbon is undecane and said alcohol is dodecyl alcohol.

9. The process as set forth in claim 1 in which said dehydrogenatable aliphatic paraffinic hydrocarbon is isobutane and said alcohol is isopentyl alcohol.

10. The process of claim 1 in which said Group VIII noble metal is platinum, said Group IVA metal is tin, and said Group IA metal is lithium, all of which are composited on alumina.

11. The process of claim 1 in which said Group VIII noble metal is palladium, said Group IVA metal is germanium, and said Group IA metal is lithium, all of which are composited on silica.

* * * * *